Figure 1:
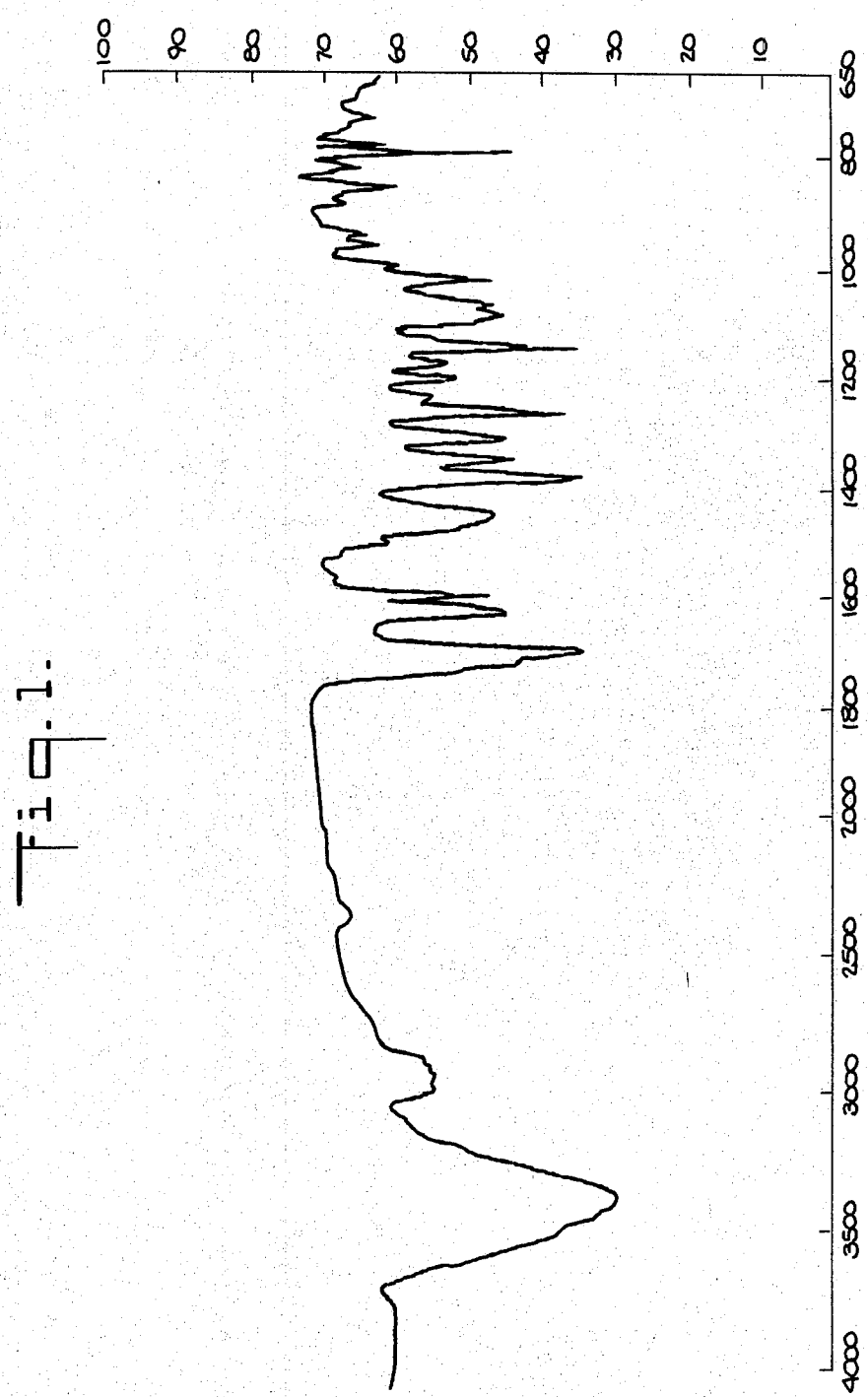

United States Patent [19]

Tomita et al.

[11] 4,340,725

[45] Jul. 20, 1982

[54] NOVEL COMPOUND DC-38-V AND PROCESS FOR PRODUCTION THEREOF

[75] Inventors: Fusao Tomita, Machida; Yuzura Matsuda, Koganei; Kunikatsu Shirahata, Machida; Keiichi Takahashi, Machida; Hirofumi Nakano, Machida; Tomoyasu Sato, Machida; Shuji Okubo, Matsudo; Nobuo Nakamura, Machida, all of Japan

[73] Assignee: Kyowa Hakko Kogyo Co., Ltd., Tokyo, Japan

[21] Appl. No.: 175,324

[22] Filed: Aug. 4, 1980

[30] Foreign Application Priority Data

Aug. 3, 1979 [JP] Japan .................................. 54-98656

[51] Int. Cl.³ .............................................. C07G 11/00
[52] U.S. Cl. ..................................... 536/1.1; 424/181; 435/118; 435/72
[58] Field of Search ........................... 536/1; 424/181; 438/118, 119, 886

[56] References Cited

U.S. PATENT DOCUMENTS

| | | | |
|---|---|---|---|
| 3,950,357 | 4/1976 | Kahan et al. | 435/119 |
| 4,062,948 | 12/1977 | Vos et al. | 536/1 |
| 4,160,861 | 7/1979 | Cole et al. | 424/181 |
| 4,269,471 | 5/1981 | Yamagishi et al. | 424/181 |

*Primary Examiner*—Hiram Bernstein
*Attorney, Agent, or Firm*—Fitzpatrick, Cella, Harper & Scinto

[57] ABSTRACT

The antibacterial compound DC-38-V is produced by culturing a microorganism belonging to the genus Streptomyces.

1 Claim, 2 Drawing Figures

NOVEL COMPOUND DC-38-V AND PROCESS FOR PRODUCTION THEREOF

BACKGROUND OF THE INVENTION

The present invention relates to a novel compound having antibacterial and anti-tumor activity, such compound being designated DC-38-V. The invention also pertains to the production of DC-38-V by culturing a microorganism belonging to the genus Streptomyces, which is capable of producing DC-38-V, in a nutrient medium, until antibacterial activity is detected in the culture liquor and then recovering DC-38-V therefrom.

Compounds which have antibacterial or anti-tumor activity are always in demand. To this end, microorganisms have been isolated from a soil sample from Kochi-shi, Japan (hereinafter referred to as 0-7 strain) and from a soil sample from Yokohama-shi, Japan (hereinafter referred to as 4916 strain); and it has been found that when the strains are cultured, a compound having antibacterial activity is produced in the culture liquor. A study of the morphological properties indicates that the microorganisms are new strains belonging to the genus Streptomyces and a study of the chemical, physical and biological properties of the active substance indicates that the compound is a new compound which is designated DC-38-V.

SUMMARY OF THE INVENTION

In accordance with the present invention, the novel compound, DC-38-V, is produced by fermentation of a microorganism belonging to the genus Streptomyces which is capable of producing DC-38-V, in a nutrient medium. At the completion of culturing when substantial antibacterial activity is detectable in the culture liquor, the compound DC-38-V is isolated from the culture liquor by known means, such as by adsorption chromatography.

DC-38-V exhibits antibacterial activity and is, therefore useful to clean and sterilize laboratory glassware and surgical instruments and may also be used in combination with soaps, detergents and wash solutions for sanitary purposes. The compound is also expected to be useful in the treatment of bacterial infections in animals due to its antibacterial properties. Moreover, as will be clear from the following description, DC-38-V, may also be useful as an anti-tumor agent in animals.

DESCRIPTION OF THE INVENTION

Figure 2:
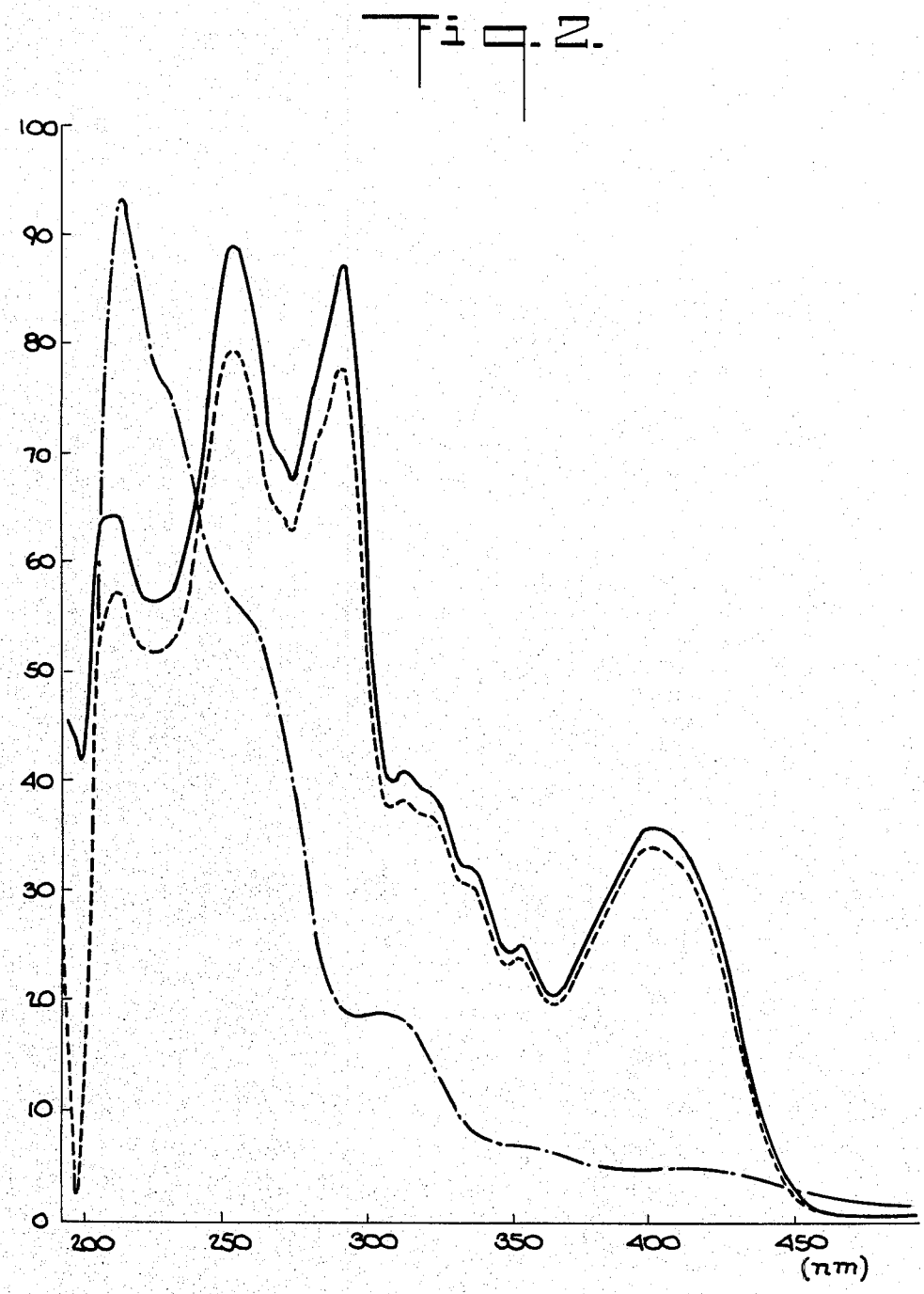

DC-38-V is a novel compound having antibacterial and anti-tumor activity. The compound is characterized by the following physicochemical properties:

(1) Melting point: 254±2° C. (decomposition).
(2) Elementary analysis: H=5.23%, C=65.69%.
(3) Infrared absorption spectrum measured in KBr tablet as illustrated in FIG. 1.
(4) Ultraviolet absorption spectrum as illustrated in FIG. 2 wherein the solid line, chain line and dotted line respectively indicate the results of the measurement in 95% ethanol; a mixed solvent of ethanol: 0.2 N NaOH (95:5 by volume); and mixed solvent of ethanol: 0.2 N HCl (95:5 by volume).
(5) Molecular weight by mass spectrometry: 494.
(6) Molecular formula: $C_{27}H_{26}O_9$.
(7) Proton magnetic resonance spectrum (PMR) of DC-38-V obtained using dimethylsulfoxide-$d_6$ as the solvent and tetramethylsilan (TMS) as the internal standard; Representative features of the spectrum were at: 9.68, 8.41, 8.06, 7.96, 7.70, 6.93, 6.19, 6.10, 5.49, 5.08, 4.83, 4.80~3.00 (many peaks are observed), 4.15(3H, m), 4.16(3H, m), 1.26(3H, m).

(8) Fluorescence spectrum: λem=494 nm (Excitation light: 428 nm).
(9) Specific optical rotation: $[\alpha]_D^{20}=-246°\pm10°$ (c=0.5, dimethylsulfoxide).

From the physicochemical properties described above, DC-38-V is considered to have the following structural formula.

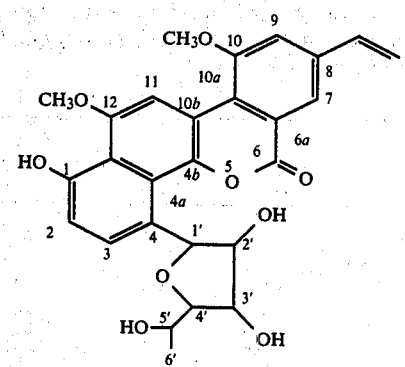

(10) Solubility.

DC-38-V is soluble in dimethylsulfoxide, dimethylformamide, pyridine and tetrahydrofuran, slightly soluble in methanol, acetone, ethyl acetate, benzene and chloroform and almost insoluble in water, petroleum ether and ether.

(11) Stability

The stability of compound is illustrated in Table 1.

TABLE 1

|  | Solid | Liquid | | |
|---|---|---|---|---|
|  |  | acidic | neutral | alkaline |
| Sun light | unstable | slightly unstable | slightly unstable | unstable |
| Shielding | stable | stable | stable | unstable |

The Rf values of DC-38-V in silica gel thin layer chromatography (TLC) using Silic AR CC-4 (trademark: Mallinchrodt Co. United States) and various developers are set forth in the following Table 2. Development is carried out at room temperature for three hours.

TABLE 2

| | Developer (V/V) | Rf |
|---|---|---|
| I. | Chloroform:Methanol (90:10) | 0.35 |
| II. | Acetone:Chloroform (67:33) | 0.60 |

DC-38-V is produced by culturing a microorganism belonging to the genus Streptomyces which is capable of producing DC-38-V in a nutrient medium, accumulating DC-38-V in the culture liquor and recovering the same therefrom.

Any microorganism may be used so long as it belongs to the genus Streptomyces and is capable of producing DC-38-V. Examples of preferred strains are the 0-7 strain and the 4916 strain mentioned above. These strains have been deposited with the culture collection of the Northern Utilization Research and Development Division, Agricultural Research Service, U.S. Department of Agriculture, Peoria, Ill. 61604 and are available to the public for the life of the patent under culture No. NRRL 11382 and 11383, respectively. These strains have also been deposited with the Fermentation Research Institute, Japan and assigned the registered number FERM-P No. 4649 and FERM-P No. 4648 respectively.

The morphological and biological properties of the 0-7 strain are illustrated below.

(A) Morphology

The formation of aerial mycelium of the strain is good on general medium for screening. The mycelium shows simple branching and is spiral.

TABLE 3

| | | Growth on various media | | | |
|---|---|---|---|---|---|
| | | Color of colony | | | Soluble |
| Medium | Growth | Surface | Reverse | G.M. | Pigment |
| Sucrose-Nitrate agar | Good, flat | Cammel (3ie) | Cammel (3ie) | Good Ash (5fe) | Coral rose (6ic) |
| Glucose-Asparagine agar | Good, flat | Oatmeal (2ec) | Egg shell (2ca) | Good Covert gray (2fe) | None |
| Glycerin-Asparagine agar | Good, raised | Oatmeal (2ec) | Egg shell (2ca) | Good Ash (5fe) | None |
| Starch-Inorganic salt agar | Good, flat | White (a) | White (a) | Good Silver gray (3fe) | None |
| Tyrosine agar | Good, raised | Light mustard tan (2ie) | Light mustard tan (2ie) | Good Natural (3dc) | None |
| Nutrient agar | Moderate, flat | Light mustard tan (2ie) | Light mustard tan (2ie) | Poor White (a) | None |
| Yeast-Malt agar | Good, flat | Light mustard tan (2ie) | Oatmeal (2ec) | Good Silver gray (3fe) | None |
| Oatmeal agar | Good, raised | Mustard tan (2lg) | Mustard tan (2lg) | Good White (a) | Dull gold (2ng) |
| Peptone-Yeast-iron agar | Moderate, flat | Bamboo (2gc) | Oatmeal (2ec) | None | None |

G.M.: Growth and color of mycelium

Spores are oval (0.4~0.5μ×0.7~0.8μ) and have a smooth surface. Ten or more spores form a chain.

The degree of growth, color of surface and reverse of colony, and soluble pigments when the 0-7 strain is cultured on various media are set forth in Table 3.

The color indications are given according to the classifications in the Color Harmony Manual, (Container Corporation of America).

(B) Physiological characteristics

The physiological characteristics of the 0-7 strain are illustrated in the following Table 4 in which the optimum temperature is determined after 5 days of culturing and the action upon milk and the decomposition of cellulose are observed after one month of culturing. The other observations are based on culturing at 27° C. for two weeks.

TABLE 4

| Utilization of Carbon Sources | |
|---|---|
| Carbon-Source | Utilization |
| D-Arabinose | − |
| D-Xylose | − |
| D-Glucose | ++ |
| D-Fructose | + |
| Sucrose | + |
| Inositol | + |
| L-Rhamnose | ++ |
| Raffinose | − |
| D-Mannitol | ++ |
| Liquefaction of gelatin | ± |

TABLE 4-continued

| Utilization of Carbon Sources | |
|---|---|
| Carbon-Source | Utilization |
| Liquefaction of milk | Negative |
| Peptonization of milk | Negative |
| Decomposition of cellulose | Weakly positive |
| Hydrolysis of starch | Positive |
| Optimum growth pH | 6.8–7.5 |
| Optimum growth temperature | 28–38° C. |
| Formation of tyrosinase | None |
| Formation of melanoid pigments | None |

From the foregoing properties, the 0-7 strain is classified as belonging to the genus Streptomyces.

According to the classification by E. Küster [Intern. J. System, Bacteriol., Vol. 22, No. 3, 139 (1972)], the strain is classified as belonging to the species, the color of the aerial mycelium of which is white; and it is determined to be similar to a strain of *Streptomyces flavescens.* The strains belonging to this species have aerial mycelia on which flexious spores are formed and utilize arabinose. On the other hand, the 0-7 strain has aerial mycelia of spiral form and does not utilize arabinose. The 0-7 strain utilizes mannitol and rhamnose as well as glucose, which the strain of *Streptomyces flavescens* utilizes little. Accordingly, the strain is determined to be a new strain and has been named *Streptomyces gilvotanareus* TOMITA.

The morphological and biological properties of the 4916 strain are illustrated below.

(A) Morphology

The formation of aerial mycelium is good on general medium for screening. The mycelium shows simple branching and is spiral.

Spores are oval (0.4~0.5μ×0.7~0.8μ) and have a spiny surface. Ten or more spores form a chain.

The degree of growth, color of surface and reverse of colony, and soluble pigments when the 4916 strain is cultured on various media are set forth in the following Table 5.

The color indications are given according to the classifications in the Color Harmony Manual, (Container Corporation of America).

TABLE 5

| Medium | Growth | Color of colony Surface | Color of colony Reverse | G.M. | Soluble Pigment |
|---|---|---|---|---|---|
| Sucrose-Nitrate agar | Moderate, flat | Bamboo (2gc) | Bamboo (2gc) | Poor White (a) | Yellow maple (3ng) |
| Glucose-Asparagine agar | Moderate, flat | Parchment (1cb) | Pearl (3ba) | Poor Pale blue (15ca) | None |
| Glycerin-Asparagine agar | Moderate, flat | Bamboo (2gc) | Bamboo (2gc) | Moderate White (a) | None |
| Starch-Inorganic salt agar | Good, flat | Oatmeal (2ec) | Light ivory (2ca) | Moderate Pale blue (15ca) | None |
| Tyrosine agar | Good flat | Mustard tan (2lg) | Light mustard tan (2ie) | Good Aqua gray (19fe) | Mustard (2le) |
| Nutrient agar | Moderate, flat | Beige (3ge) | Light beige (3ec) | None | Dull gold (2ng) |
| Yeast-Malt agar | Good, flat | Light mustard tan (2ie) | Light mustard tan (2ie) | Good Aqua gray (19fe) | None |
| Oatmeal agar | Good, flat | Oatmeal (2ec) | Light mustard tan (2ie) | Good Aqua gray (19fe) | 3ge |
| Peptone-Yeast-iron agar | Poor, raised | Oatmeal (2ec) | Bamboo (2gc) | None | None |

G.M.: Growth and color of mycelium

(B) Physiological Characteristics

The physiological characteristics of the 4916 strain are illustrated in Table 6 in which the optimum temperature is determined after 5 days of culturing and the action upon milk and the decomposition of cellulose are observed after one month of culturing. The other observations are based on culturing at 27° C. for two weeks.

TABLE 6

| Utilization of Carbon Sources | |
|---|---|
| Carbon Source | Utilization |
| D-Arabinose | − |
| D-Xylose | + |
| D-Glucose | + |
| D-Fructose | ++ |
| Sucrose | ++ |
| Inositol | ++ |
| L-Rhamnose | ++ |
| Raffinose | ++ |
| D-Mannitol | ++ |
| Liquefaction of gelatin | ± |
| Liquefaction of milk | Positive |
| Peptonization of milk | Negative |
| Decomposition of cellulose | Weakly positive |
| Hydrolysis of starch | Positive |
| Optimum growth pH | 6.8–7.5 |
| Optimum growth temperature | 28–38° C. |
| Formation of tyrosinase | None |
| Formation of melanoid pigment | None |

From the foregoing properties, the 4916 strain is classified as belonging to the genus Streptomyces.

According to the classification by E. Küster [Intern. J. System. Bacteriol., Vol. 22, No. 3, 139 (1972)], the strain belongs to the species, the color of aerial mycelia of which is gray; and the strain is determined to be similar to the strain of *Streptomyces griseoincarnatus*. However, there is a disclosure in Intern. J. System. Bacteriol., Vol. 18, No. 4, 328 (1968) by E. B. Shirling and D. Gottlieb that *Streptomyces griseoincarnatus* utilizes arabinose and cannot utilize raffinose. On the other hand, the 4916 strain does not utilize arabinose but utilizes raffinose. Further, it is described in the literature mentioned above that the *Streptomyces griseoincarnatus* strain produces an orange pigment, but the 4916 strain produces a yellow pigment. Accordingly, the species of the 4916 strain does not belong to *Streptomyces griseoincarnatus*. Thus, the 4916 strain is determined to be a new strain and has been named *Streptomyces griseologilbus* TOMITA from the color of the mycelia.

As is the case with other strains of the Actinomycetes, the microorganisms useful in carrying out the present invention can be mutated by artificial means such as ultraviolet irradiation, $Co^{60}$ irradiation, X-ray irradiation and the action of various mutagens such as N-methyl-N'-nitro-N-nitrosoguanidine, etc. Accordingly, any strain, even if thus mutated, is contemplated as appropriate for the present invention insofar as it has the ability to produce the compound DC-38-V.

Generally, conventional methods for culturing Actinomycetes may be employed in the process of the present invention. Thus, various nutrient sources may be used for the culture medium. Appropriate carbon sources include glucose, starch, dextrin, mannose, fructose, sucrose, lactose, xylose, arabinose, mannitol, molasses, etc. either alone or in combination. Hydrocarbons, alcohols, organic acids, etc. may also be used depending upon the assimilability possessed by the microorganisms to be used. As inorganic and organic nitrogen sources, ammonium chloride, ammonium sulfate, ammonium nitrate, sodium nitrate, urea, may be used either alone or in combination or natural nitrogen such as peptone, meat extract, yeast extract, dry yeast, corn steep liquor, soybean powder, casamino acid, etc. are appropriate. If necessary, inorganic salts such as sodium chloride, potassium chloride, magnesium sulfate, calcium carbonate, potassium dihydrogen phosphate, dipotassium hydrogen phosphate, ferrous sulfate, calcium chloride, manganese sulfate, zinc sulfate, copper sulfate, etc. may be added to the medium. Moreover, organic and inorganic materials such as vitamin $B_1$, biotin, etc. which promote the growth of the particular strain and enhance the production of DC-38-V may be added to the medium.

A liquid culturing method, particularly a submerged stirring culturing method is most suitable. Culturing temperature is 25°–40° C., preferably 28°–38° C., and the pH is controlled at 4–10, preferably 6–8 with aqueous ammonia, ammonium carbonate solution, etc. Usually, after 1 to 7 days of liquid culturing, DC-38-V is formed and accumulated in the culture liquor. When the yield of DC-38-V in the culture liquor reaches a maximum, culturing is discontinued and the desired product is isolated and purified from the culture liquor after the microbial cells have been removed by filtration, etc.

Isolation and purification of DC-38-V are carried out by methods usually used for the isolation and purification of microbial metabolic products from a culture liquor. For example, the cell-free culture filtrate (pH 6.0) is passed through a column packed with nonionic porous resin, such as HP-20 (trademark, Mitsubishi Chemical Industries) to adsorb active principles; and the active principles are desorbed using methanol, acetone, ethyl acetate, or the like. The resultant eluate is concentrated to dryness and the residue is dissolved in chloroform. Then the solution is passed through a column packed with active carbon and elution is carried out with an organic solvent such as ethyl acetate. The eluate is concentrated to dryness and the residue is dissolved in chloroform. The solution is then passed through a column packed with silica gel suspended in chloroform to adsorb active principles. Then chloroform is passed through the column to remove impurities.

Elution is then carried out with a mixed solvent of chloroform and methylisobutylketone (50:50 by volume) to elute DC-38-V. Fractions containing DC-38-V are collected and concentrated to dryness to obtain the active substance. Recrystallization of the substance from 80% acetone solution is repeated to obtain the product in crystalline form.

Isolation and purification of the desired compound from microbial cells are carried out as follows. The cells are extracted with acetone and the extract is concentrated to dryness. The resultant residue is dissolved in chloroform and then the solution is subjected to chromatography using silica gel and recrystallization in the same manner as in the above purification method of DC-38-V from filtrate to obtain crystals of DC-38-V.

The biological properties of DC-38-V are illustrated below.

The in vitro antibacterial spectra of DC-38-V determined by the agar dilution method (pH 7.0) is illustrated in the following Table 7.

TABLE 7

| Minimum Inhibitory Concentration (μg/ml) | |
|---|---|
| Microorganism | MIC |
| *Staphylococcus aureus* ATCC 6538 P | 0.0375 |
| *Bacillus subtilis* No. 10707 | 0.0375 |
| *Klebsiella pneumoniae* ATCC 10031 | >75 |
| *Escherichia coli* ATCC 26 | 18.75 |
| *Shigella sonnei* ATCC 9290 | >75 |
| *Salmonella typhosa* ATCC 9992 | >75 |

The acute toxicity ($LD_{50}$) of DC-38-V is >1000 mg/kg when the test compound is administered intraperitoneally to mice.

The anti-tumor activity of DC-38-V is as follows:

(1) Effect on sarcoma 180 solid tumor

Six male ddY-strain mice having a weight of about 20 g are used for each group as test animals; and $5 \times 10^6$ cells of Sarcoma 180 ascites tumor are implanted subcutaneously in the animals. After 24 hours following implantation, 0.2 ml phosphate buffered saline (PBS) containing DC-38-V in various concentrations is administered intraperitoneally.

Since DC-38-V is almost insoluble in water, 25 mg of Tween 80 is mixed with 10 mg of DC-38-V and PBS is added to the mixture to obtain a suspension. Then the suspension is diluted with PBS to obtain suspensions having various concentrations of test compound.

As a control, PBS solution containing Tween 80 is used. The test animals are not affected by the control solution. PBS comprises 0.8 g/dl NaCl, 0.02 g/dl KCl, 1.15 g/dl $Na_2HPO_4$, and 0.02 g/dl $KH_2PO_4$ (pH 7.2).

For comparison, 0.2 ml PBS solution containing mitomycin C is administered to a group of animals intraperitoneally at the same time as the test compound.

Seven days after implantation, the average tumor volume ($mm^3$) and T/C (T: average tumor volume of the group treated with the test compound, C: that of control) are determined. The results are shown in the following Table 8.

TABLE 8

| Test Compound | Dosage (mg/kg) | V ($mm^3$) | T/C |
|---|---|---|---|
| Control | — | 1,420 | — |
| DC-38-V | 100 | 1,085 | 0.76 |
| DC-38-V | 200 | 874 | 0.62 |
| DC-38-V | 400 | 562 | 0.40 |
| Mitomycin C | 4.2 | 529 | 0.37 |

V: average tumor volume (2) Effect on Lymphocytic leukemia P-388 tumor

Five male $CDF_1$ mice having a weight of about 22 g are used for each group as test animals; and $1 \times 10^6$ cells of Lymphocytic leukemia P-388 tumor are implanted intraperitoneally in the test animals. Twenty-four hours following implantation, 0.2 ml PBS solution containing DC-38-V in various concentrations is administered intraperitoneally.

For comparison, 0.2 ml PBS solution containing mitomycin C is administered to a group of test animals intraperitoneally at the same time as the test compound.

The mean survival time (MST: days) and increased life span (ILS: %)

$$ILS\ (\%) = \frac{MST \text{ of the groups administered with test compound}}{MST \text{ of the control}} \times 100$$

after implantation are shown in the following Table 9.

TABLE 9

| Test Compound | Dosage (mg/kg) | MST (days) | ILS (%) |
|---|---|---|---|
| Control | — | 9.7 | — |
| DC-38-V | 50 | 13.4 | 138 |
| DC-38-V | 100 | 14.5 | 141 |
| DC-38-V | 200 | 16.0 | 155 |
| DC-38-V | 400 | 16.7 | 162 |
| Mitomycin C | 4.2 | 16.5 | 160 |

(3) Effect on MH 134 ascites tumor

Six male C3H-strain mice having a weight of about 20 g are used for each group as test animals; and $5 \times 10^6$ cells of MH 134 ascites tumor are implanted in the animals intraperitoneally. After 24 hours following implantation, 0.2 ml PBS suspension containing DC-38-V in various concentrations is administered intraperitoneally.

For comparison, 0.2 ml PBS solution containing mitomycin C is administered to a group of animals intraperitoneally at the same time as the test compound.

The MST and ILS after implantation are shown in the following Table 10.

TABLE 10

| Test compound | Dosage (mg/kg) | MST (days) | ILS (%) | LTS ($\geq 40$ days) |
|---|---|---|---|---|
| Control | 0 | 17.1 | — | 0/6 |
| DC-38-V | 100 | >31.5 | >184 | 3/6 |
| DC-38-V | 200 | >53.0 | >310 | 6/6 |
| DC-38-V | 400 | >39.5 | >231 | 2/6 |
| Mitomycin C | 1.05 | 18.1 | 106 | 0/6 |
| Mitomycin C | 2.1 | 19.8 | 116 | 0/6 |
| Mitomycin C | 4.2 | 20.5 | 120 | 0/6 |
| Mitomycin C | 8.4 | 9.4 | 55 | 0/6 |

LTS: Long term survivors

(4) Effect on Ehrlich ascites carcinoma

Five male ddY-strain mice having a weight of about 20 g are used for each group as test animals; and $5 \times 10^6$ cells of Ehrlich ascites carcinoma are implanted in the animals intraperitoneally. After 24 hours following implantation or once a day for five days from 24 hours after implantation, 0.2 ml PBS suspension containing DC-38-V in various concentrations is administered intraperitoneally.

The MST and ILS after implantation are shown in Table 11 and Table 12.

For comparison, mitomycin C is used as test compound.

TABLE 11

| Test compound | Dosage (mg/kg) | MST (days) | ILS (%) | LTS ($\geq 60$ days) |
|---|---|---|---|---|
| Control | — | 15.2 | | 0/5 |
| DC-38-V | 50 × 1 | 17.4 | 114 | 0/5 |
| DC-38-V | 100 × 1 | >30.6 | >202 | 1/5 |
| DC-38-V | 200 × 1 | >40.2 | >264 | 2/5 |
| DC-38-V | 400 × 1 | >41.8 | >275 | 2/5 |
| Mitomycin C | 2.1 × 1 | 18.6 | 122 | 0/5 |
| Mitomycin C | 4.2 × 1 | >30.8 | >203 | 1/5 |
| Mitomycin C | 5.6 × 1 | 18.6 | 122 | 0/5 |

TABLE 12

| Test compound | Dosage (mg/kg) | MST (days) | ILS (%) | LTS ($\geq 60$ days) |
|---|---|---|---|---|
| Control | — | 15.8 | | 0/5 |
| DC-38-V | 25 × 5 | >49.8 | >315 | 3/5 |
| DC-38-V | 50 × 5 | >56.6 | >358 | 4/5 |
| DC-38-V | 100 × 5 | >60 | >380 | 5/5 |

As is evident from the foregoing, DC-38-V is useful both as an anti-tumor agent and as an antibacterial agent in animals.

The compound may be employed in capsule form, tablet, powders, solution, suspension or elixirs. They may be administered orally, intravenously, intraperitoneally or intramuscularly.

In general, a daily dosage consists of 3~12 mg/kg/day of active ingredient for the continuous intraperitoneal or intravenous administration and 24~48 mg/kg/once of active ingredient for the interval intravenous or intraperitoneal administration.

Certain specific embodiments of the present invention are illustrated by the following representative examples wherein the presence of DC-38-V is monitored by bio-assay using *Bacillus subtilis* No. 10707.

EXAMPLE 1

In this example, *Streptomyces gilvotanareus* 0-7, NRRL 11382, is inoculated into a 2 L-Erlenmeyer flask containing 300 ml of seed medium comprising 4 g/L KCl, 0.5 g/L $MgSO_4.7H_2O$, 1.5 g/L $KH_2PO_4$, 5.0 g/L $(NH_4)_2SO_4$, 20 g/L sucrose, 10 g/L fructose, 10 g/L glucose, 5.0 g/L corn steep liquor and 20 g/L $CaCO_3$ (pH 7.0) and cultured at 30° C. for 48 hours with stirring (220 r.p.m.). Then, 0.75 L of the thus obtained seed culture is transferred to a 30 L-jar fermenter containing 15 L of a fermentation medium comprising 70 g/L fructose, 10 g/L soluble starch, 5 g/L yeast extract, 10 g/L ammonium sulfate, 8 g/L potassium chloride, 1 g/L magnesium sulfate, 0.2 g/L $K_2HPO_4$, 40 mg/L $FeSO_4.7H_2O$ and 3 mg/L $ZnSO_4.7H_2O$. The pH of the medium is adjusted to 7.3 with NaOH before sterilization. Culturing is carried out at 30° C. with aeration and agitation (15 L/min, 250 r.p.m.) for 72 hours without controlling the pH of the medium.

The resulting culture liquor is filtered to obtain 13 L of filtrate. The filtrate is passed through a column packed with 1 L of non-ionic porous resin HP-10 (trademark, Mitsubishi Chemical Industries) to adsorb the active principles. Then the resin is washed with 2 L of water and 2 L of 50% (V/V) methanol solution to remove the impurities. Elution is carried out with acetone and 1 L of the acetone fractions is concentrated to dryness to obtain a residue which is then dissolved in 10 ml of chloroform.

The insoluble matter is filtered off and the chloroform solution is subjected to chromatography using silica gel with the extract from microbial cells described below.

About 200 g of microbial cells (wet weight) are suspended in 5 L of acetone to extract the desired compound. The resultant extract is concentrated to dryness and the residue is dissolved in about 10 ml of chloroform which is then filtered to remove the insoluble matter. The resultant chloroform solution is combined with that obtained from the filtrate to obtain about 35 ml solution. The solution is charged to a column packed with 500 ml silica gel, Silic AR CC-4 (trademark, Mallinckrodt Co., United States) suspended in chloroform and washed with about 2 L of chloroform.

Then elution is carried out with a mixed solvent of chloroform and methylisobutylketone (50:50 by volume) to elute the fractions containing DC-38-V. These fractions are concentrated and recrystallization of the residue from 80% acetone solution is repeated to obtain 0.23 g of crystals. The physicochemical, biological and medicinal properties of the crystals are as described above.

EXAMPLE 2

In this example, the same fermentation procedures as described in Example 1 are repeated except that the composition of the fermentation medium is 30 g/L glucose, 10 g/L soluble starch, 10 g/L Pharma media (trademark, Traders Oil Mill Co. U.S.A.), 1 g/L $K_2HPO_4$, 1 g/L $MgSO_4.7H_2O$, 3 g/L NaCL, 70 mg/L $CuSO_4.5H_2O$, 10 mg/L $FeSO_4.7H_2O$, 8 mg/L $MnCl_2.4H_2O$, 2 mg/L $ZnSO_4.7H_2O$ and 0.006 mg/L $CoCl_2.6H_2O$ (pH 7.0 adjusted with NaOH before sterilization).

The same purification procedures as described in Example 1 are repeated except that a mixed solvent of n-hexane and ethyl acetate (80:40 by volume) as developer is used instead of a mixed solvent of chloroform and methylisobutylketone (50:50 by volume) to obtain 2.0 g of DC-38-V as yellowish needle crystals.

EXAMPLE 3

In this example, *Streptomyces griseologilbus* 4916, NRRL 11383 is used as the seed strain.

The same procedures as described in Example 1 are repeated to obtain 0.11 g of DC-38-V.

EXAMPLE 4

In this example, *Streptomyces griseologilbus* 4916 NRRL 11383 is used as the seed strain.

The same procedures as described in Example 2 are repeated to obtain 1.5 g of DC-38-V as yellowish needle crystals.

EXAMPLE 5

In this example, *Streptomyces gilvotanareus* 0-7, NRRL 11382 is used as the seed strain, and the productivity of DC-38-V is examined using various carbon sources.

The same seed medium and the same fermentation medium except carbon source as described in Example 1 are used.

The strain is inoculated in a 2 L-Erlenmeyer flask provided with baffles containing 300 ml medium. Culturing is carried out at 30° C. with shaking (220 r.p.m.) for 5 days.

The thus obtained culture filtrate and acetone extract of microbial cells are subjected to thin layer chromatography using silica gel. The corresponding spot is collected and is extracted with acetone. Then the antibacterial activity of the resultant extract is determined using *Bacillus subtilis* 10707. The results are shown in Table 13.

TABLE 13

| Production of DC-38-V by using various carbon sources | | |
|---|---|---|
| Carbon source | (g/l) | Production (μg/ml) |
| Sucrose | (70) | 101 |
| Glucose | (70) | 105 |
| Fructose | (70) | 109 |
| Lactose | (70) | 100 |
| Glucose + Xylose | (10) (40) | 98 |
| Glucose + Arabinose | (10) (40) | 102 |
| Glucose + Mannitol | (10) (40) | 94 |

What is claimed is:

1. A compound of the formula

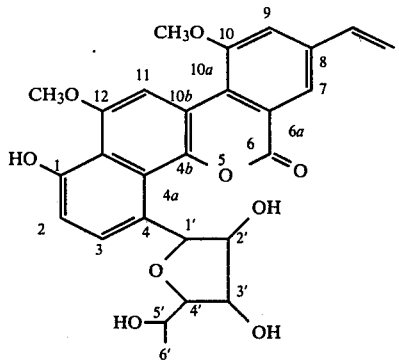

characterized by an infrared absorption spectrum substantially as shown in FIG. 1, an ultraviolet absorption spectrum substantially as shown in FIG. 2, a molecular weight of 494 determined by mass spectrometry, and a molecular formula of $C_{27}H_{26}O_9$.

* * * * *